United States Patent [19]

Nakaji

[11] Patent Number: 4,907,306
[45] Date of Patent: Mar. 13, 1990

[54] SUPINE SUPPORT DEVICE AND METHOD FOR TREATMENT AND PREVENTION OF MALOCCLUSION OF THE TEETH

[76] Inventor: Norman K. Nakaji, 2440 Statesville Blvd., Salisbury, N.C. 28144

[21] Appl. No.: 194,398

[22] Filed: May 16, 1988

Related U.S. Application Data

[63] Continuation-in-part of Ser. No. 115,694, Nov. 2, 1987, abandoned.

[51] Int. Cl.⁴ .............................................. A47G 9/00
[52] U.S. Cl. .......................................... 5/436; 5/437
[58] Field of Search ................... 5/431, 432, 434, 436, 5/437, 419, 435; 128/70, 76 R, 78, 845, 846, 869, 870, 861; 297/457, 377; 269/328

[56] References Cited

U.S. PATENT DOCUMENTS

| 3,276,046 | 10/1966 | Capelli | 5/436 |
| 3,648,308 | 3/1972 | Greenawalt | 5/436 |
| 3,729,752 | 5/1973 | Huggins | 128/870 |
| 4,024,861 | 5/1977 | Vincent | 128/870 |
| 4,259,757 | 4/1981 | Watson | 5/434 |
| 4,736,736 | 4/1988 | Moers et al. | 5/436 |
| 4,759,089 | 7/1988 | Fox | 5/436 |
| 4,805,603 | 2/1989 | Cumberland | 5/441 |

FOREIGN PATENT DOCUMENTS

| 2609616 | 7/1988 | France | 5/434 |
| 1590583 | 6/1981 | United Kingdom | 5/432 |

Primary Examiner—Gary L. Smith
Assistant Examiner—Eric K. Nicholson
Attorney, Agent, or Firm—Shefte, Pinckney & Sawyer

[57] ABSTRACT

A wedge-shaped pillow having recessed areas for a user's torso and head to promote supine sleeping as a beneficial deterrent to orthodontic problems and to generally promote sleeping comfort.

12 Claims, 3 Drawing Sheets

SUPINE SUPPORT DEVICE AND METHOD FOR TREATMENT AND PREVENTION OF MALOCCLUSION OF THE TEETH

CROSS REFERENCE TO RELATED APPLICATION

This is a continuation-in-part of co-pending U.S. patent application Ser. No. 115,694, filed Nov. 2, 1987, entitled "Supine Support Device," now abandoned.

BACKGROUND OF THE INVENTION

The present invention relates to support devices, such as pillows and the like, used during sleeping, resting and similar periods of general inactivity in a recumbent or reclining posture. More particularly, the present invention relates to a support device of the foregoing type adapted to constrain the user to lie in a supine position.

It is of course widely recognized that differing people tend to naturally assume widely varying postures when in a recumbent position during sleeping and other resting periods. Basically, such diverse recumbent positions may be loosely groups into three categories, postures wherein the individual lies in a prone position, i.e. with the abdominal area essentially downward and the face to one side, postures wherein the individual lies in a sidewise position, i.e. with one side of the body essentially downward and the face to one side, and postures wherein the individual lies in a supine position, i.e. essentially with the back downward and the face upward. Conventional wisdom has generally assumed that an individual's normal recumbent resting position is primarily a matter of personal preference and natural inborn proclivities, although childhood learning and training may also be influential.

Little attention is known to have been given to the ramifications of differing sleeping and resting positions on the individual's health and general well-being. It has now been discovered that in fact a person's normal sleeping position may directly affect the occlusion of the teeth. Particularly, it has been found that a greater incidence of malocclusion tends to occur in persons who normally sleep in a prone or sidewise position wherein persons typically hug or otherwise press a pillow against the face transferring pressure from the shoulder, upper arm, forearm or hand to the face, jaws and teeth causing the lower jaw to assume an unnatural relationship with respect to the upper jaw. Malocclusion in the form of rotated, overlapping teeth, temporomandibular joint (TMJ) dysfunction, overbites, crossbites and midline deviations have been found to be directly related to habitual "pillow hugging" in a sidewise or prone sleeping position. As a result, individuals who sleep in a prone or sidewise position are considerably more likely to require orthodontic treatment and, moreover, orthodontic correction of malocclusion in such persons normally requires a longer treatment period, e.g. six months to one year longer. Further, orthodontic correction may be less likely to achieve long-term beneficial results in persons who sleep in a prone or sidewise position in that the malocclusion will tend to reoccur if that person discontinues retainer wear.

It has also been found that attempts to relieve harmful pressures on the teeth during sleeping by attempting to prevent pillow hugging are generally unsuccessful. Thus, sleeping without a pillow, with a pillow under a fitted bedsheet, with the head and shoulders elevated, or with various commercially available orthopedic pillows has not been found to significantly affect the incidence of malocclusion.

Accordingly, at least from the standpoint of promoting proper occlusion of the masticatory surfaces of the maxillary and mandibular teeth, a supine rather than prone or sidewise sleeping positions should be encouraged. Furthermore, it is believed that a supine sleeping position is of greater comfort and promotes a more restful and beneficial sleep, so that the overall health and well-being of an individual will also be benefited.

SUMMARY OF THE INVENTION

It is accordingly an object of the present invention to provide a support device and method which are particularly adapted for constraining a user to lie in a supine position during sleeping, resting and similar periods of general inactivity for treatment and prevention of malocclusion of the teeth.

Briefly described, the support device of the present invention basically comprises a main body adapted for supporting a user's torso and head when supine. The main body has an upper surface formed with a relatively elevated marginal region bordering a relatively recessed user support region which generally conforms in shape to the human torso and head. In this manner, a user is enabled to comfortably lie supine with the user's torso and head within the recessed user support region, while the elevated marginal region acts to resist any tendency of the user to turn from the supine position. As a result, the device promotes the natural development of the occlusion of the user's teeth by deterring the user from sleeping and resting in prone and sidewise positions wherein the user's jaws may assume an unnatural relationship.

In the preferred embodiment of the present invention, the support device is constructed as a pillow with the main body having a lower surface for resting disposition on a generally horizontal support surface suitable for sleeping and resting such as a mattress, bed or the like and with the upper surface of the main body being cushioned and extending at an acute angle with respect to the lower surface for dispostion at an upward incline with respect to horizontal. The recessed user support region of the upper surface has a torso support area and a head support area generally conforming in shape to the human torso and head with a cervical support area intermediate the torso and head support areas relatively elevated therefrom to provide support to the user's neck when lying supine with the user's torso and head within the recessed torso and head support areas. The main body of the pillow is fabricated with a first substantially wedge-shaped body member which forms the lower surface of the main body, a second substantially planar body member secured in superposed relation to the first body member for forming the user support region, a third substantially planar body member secured in superposed relation to the second body member and having an opening formed therethrough in the general shape of the human torso and head for forming the elevated marginal region and defining the recessed user support region, and a fourth body member secured in superposed relation to the second body member intermediate the torso and head support areas of the user support region for forming the cervical support area. Preferably, the main body of the pillow is covered by a suitable upholstery material.

The support device may be provided with one or more support members which are selectively attachable to and detachable from the upper surface of the main body for selectively adjusting the recessed user support region to the user. For this purpose, a cervical support member may be selectively attachable to and detachable from the recessed user support region at the cervical support area between the torso and head support areas and, similarly, a lumbar support member may be selectively attachable to and detachable from the recessed user support region at a lumbar support portion of the torso support area. Preferably, each of the cervical and lumbar support members are selectively positionable to some extent within their respective mounting areas to suit the user's particular preferences and needs. An elongated auxiliary cushion member may also be provided for selective attachment to and detachment from the upper surface of the main body within the recessed user support region to extend substantially along the full extent of the marginal region adjacent the user support region, to permit the selective adjustment of the size of the user support region to be compatible with users of varying sizes. Preferably, the main body of the support device and each of the support members have mating fastener members thereon, e.g. VELCRO fastener strips, to provide for attachment, positioning and detachment of the respective support members as described.

According to the method of the present invention, malocclusion of a patient's teeth is treated and prevented by constraining the patient to lie in a supine position during sleeping. Basically, the method contemplates providing a support device of the above-described type and causing the patient when sleeping to lie supine within the recessed user support region of the device wherein the elevated marginal region resists any tendency of the patient to turn from the supine position, thereby permitting the occclusion of the patient's teeth to develop naturally without being affected by unnatural relative disposition of the patient's jaws often caused by sleeping in prone and sidewise positions. Preferably, the support device is inclined in use upwardly with respect to horizontal to provide the patient with a sense of balance and stability, for example by forming the support device of a wedge shape as described. To avoid possible stress on the patient's lower back, the patient's legs may be supported with an auxiliary cushion or the like. Similarly, the method may include providing supplementary support for the patient's neck and lower back in the cervical and lumbar areas.

DETAILED DESCRIPTION OF THE PREFERRED EMBODIMENT

Figure 1:
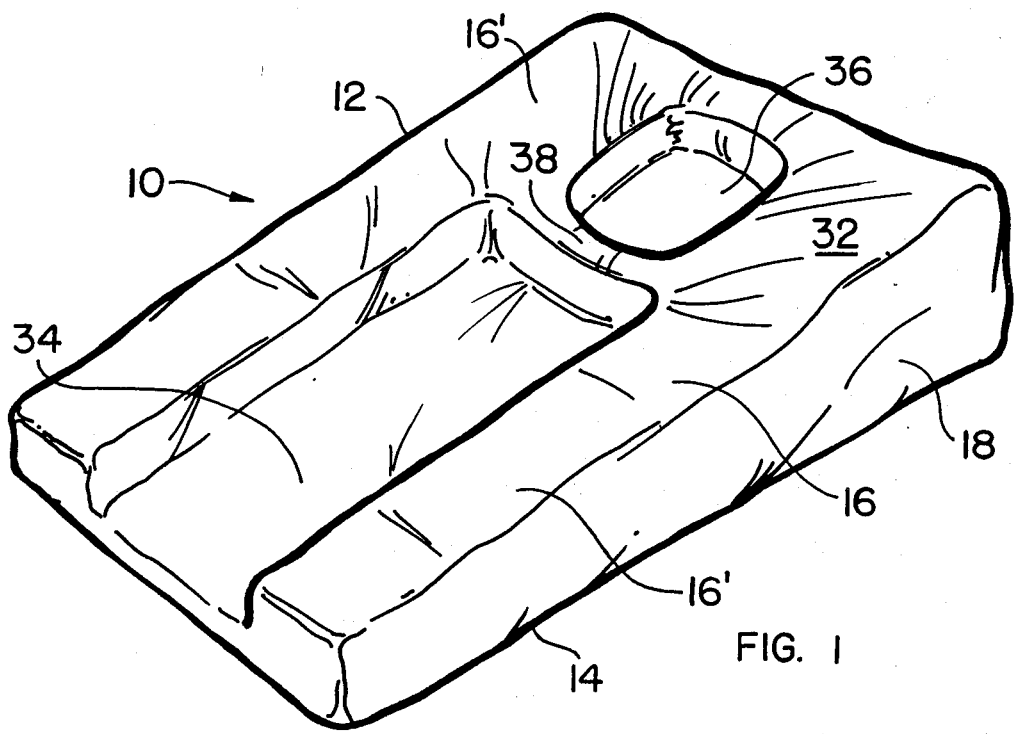
FIG. 1 is a perspective view of one preferred embodiment of the supine support device of the present invention.
Figure 2:
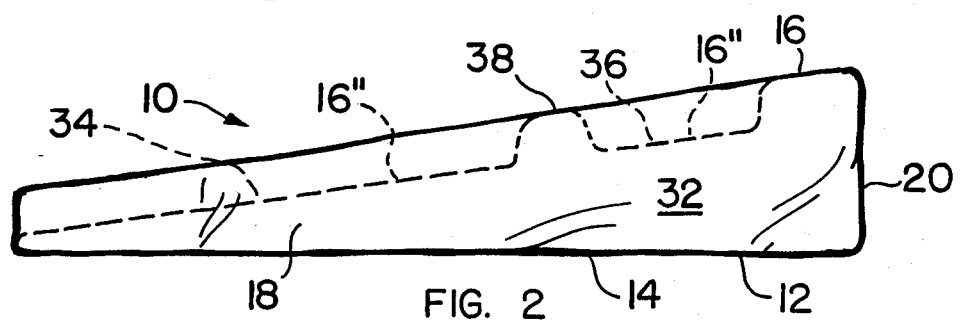
FIG. 2 is a right side elevational view thereof.
Figure 3:
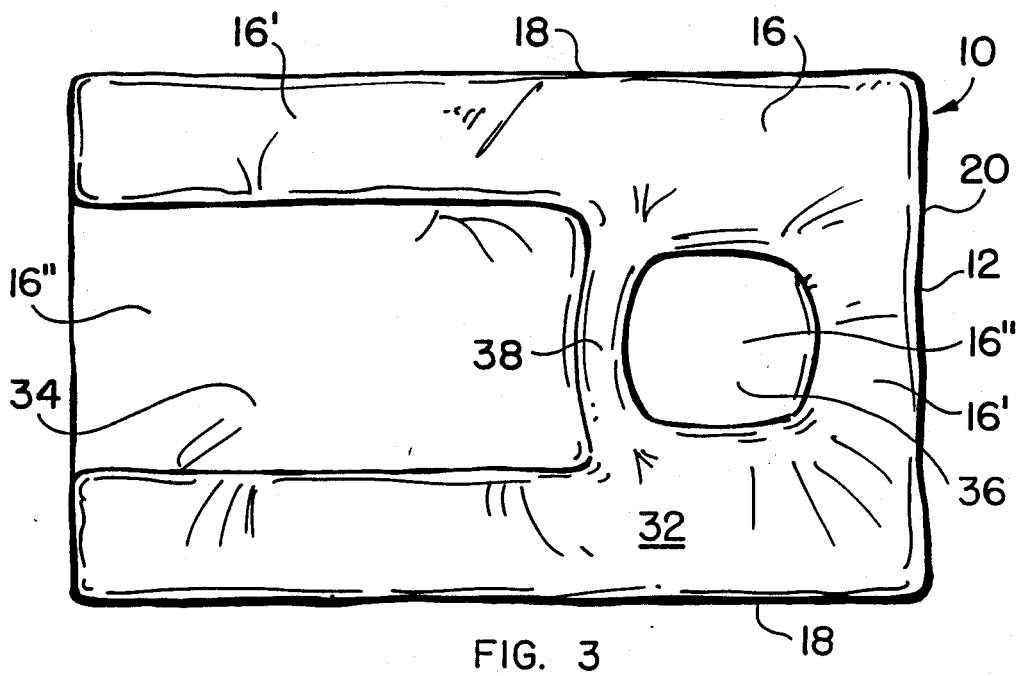
FIG. 3 is a top plan view thereof.

Referring now to the accompanying drawings and initially to FIG. 1, a supine support pillow according to the preferred embodiment of the present invention is indicated generally at 10. The pillow 10 has a main body 12 which is generally of an overall wedge-like shape having a substantially rectangular planar lower surface 14 (FIG. 2), a correspondingly rectangular upper surface 16 oriented at an acute angle with respect to the lower surface 14, and a pair of triangular side surfaces 18 and a rectangular back surface 20 (FIGS. 2 and 3) which extend essentially perpendicularly between the lower and upper surfaces 14,16.

Figure 4:
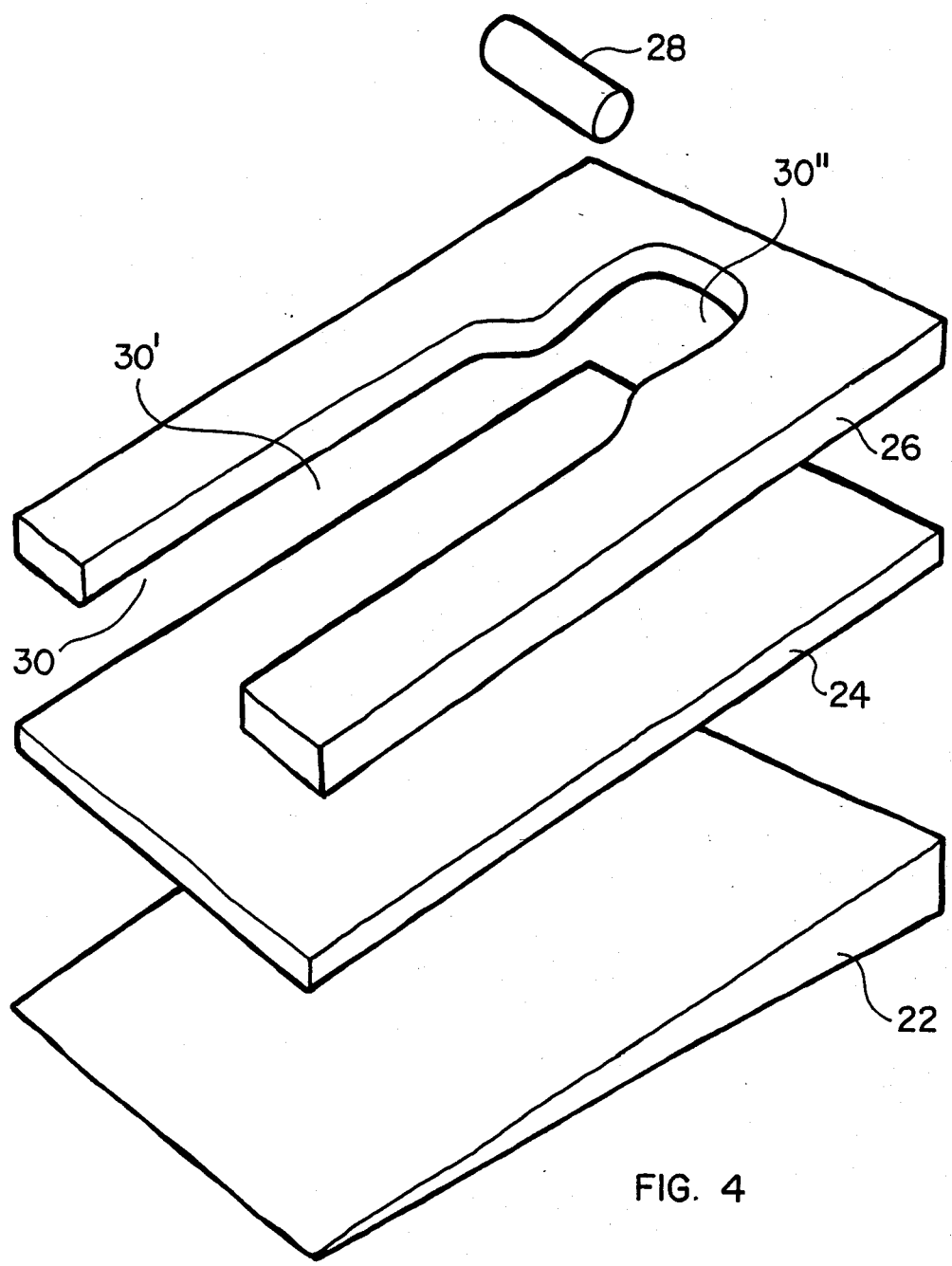
FIG. 4 is an exploded view of the main body thereof.

The main body 12 is fabricated of a suitable cushioning material, which may preferably be the densified batting material currently manufactured and sold by the William T. Burnette Company located in Statesville, North Carolina. As seen in FIG. 4, the main body 12 is basically formed of four body members 22,24,26,28, each preferably formed of the selected cushioning material. The first body member 22 is substantially of a triangular wedge-like shape, while the second bdy member 24 is of a substantially rectangular parallelipiped configuration and is secured in superposed relation to the upper face of the wedge-shaped body member 22, in a suitable manner such as by stitching, adhesive or other appropriate means. The third body member 26 is of a substantially identical rectangular parallelipiped configuration as the body member 24, but is formed lengthwise with an opening 30 therethrough of a shape generally conforming in outline to the normal shape of the human upper torso and head. The third body member 26 is secured in superposed relation to the upper face of the second body member 24 in similar fashion to its securement to the wedge-shaped body member 22, with the torso area 30' of the opening at the declining lengthwise end of the second body member 24 and the head area 30" of the opening 30 at the opposite inclining end of the second body member 24. The fourth body member 28 is of a generally cylindrical shape secured to the upper face of the second body member 24 to extend generally co-extensively with the third body member 26 transversely intermediate the torso and head areas 30',30" of its opening 30. The main body 12 is preferably upholstered with a suitable textile fabric or other appropriate upholstery material 32.

By the above-described construction, the underside of the first body member 22 of the pillow 10 forms the lower surface 14 of its main body 12 to be adapted for disposition on a generally horizontal support surface such as a mattress, bed, floor or the like. The upper faces of the second and third body members 24,26 form the upper surface 16 of the main body 12 of the pillow 10, the third body member 26 forming a relatively elevated marginal region 16' which borders and defines a relatively recessed user support region 16" formed by the upwardly exposed central area of the second body member 24. The recessed region 16" of the upper surface 16 of the pillow 10 is basically divided into a torso support area 34 defined within the torso portion 30' of the opening 30 in the third body member 26 and a head support area 36 defined within the head portion 30" of the opening 30 in the body member 26, separated by a relatively elevated cervical support area 38 formed by the fourth body member 28.

In use, the pillow 10 is placed with its lower surface 14 as aforedescribed on a bed or other suitable generally horizontal surface of which a user wishes to lie for sleeping or resting, whereby the cushioned upper surface 16 extends from its torso support area 34 to its head support area 36 at an acute upward incline with respect to horizontal. The user may then comfortably lie supine on the bed or other support surface with the user's torso and head resting within the recessed torso and head support areas 34,36 while the cervical support area 38 provides support to the user's neck. The relative elevation of the marginal region 16' formed by the third body member 26 makes it difficult and uncomfortable for the user to turn first to a sidewise or prone position, at least without first moving to a sitting position and awakening, and thereby resists any such tendency of the user so as to maintain the user in the desired supine resting position. The slight inclination provided by the wedge shape of the pillow 10 provides the user with an increased sense of balance and stability in comparison to a substantially horizontal supine position, which further promotes user comfort in the supine position and aids in preventing any user tendency to turn or move therefrom. If necessary or desirable, an auxiliary cushion or pillow may be placed under the user's legs to relieve any possible stress on the lower back area.

In this manner, users may become conditioned to sleeping and otherwise resting in a supine position with a high degree of comfort and minimal disruption of normal sleep patterns. As a highly beneficial result, the occlusion of each user's teeth will be enabled to develop naturally. Long-term use of the pillow of the present invention will thereby minimize and, in at least some cases, eliminate, the need for orthodontic treatment, particularly if use is begun during early childhood. For users who nevertheless require orthodontic treatment, use of the present pillow will shorten the time period required for correction of orthodontic problems by six months' to one year's time and thereafter will prevent or at least minimize any tendency of such problems to return. For sake of comfort, convenience and to promote optimal results, it is anticipated that the pillow of the present invention may be fabricated in varying sizes to accommodate users of all ages and physical sizes. As necessary or desirable, the present pillow may be provided with a restraining strap to assist the user during the initial periods of use. Moreover, apart from the foregoing advantages of the present pillow, it is also anticipated that the pillow will provide enhanced sleeping comfort in comparison to prone sleeping positions to promote more restful and beneficial sleep habits for all users, whether or not orthodontic problems are present.

Figure 5:
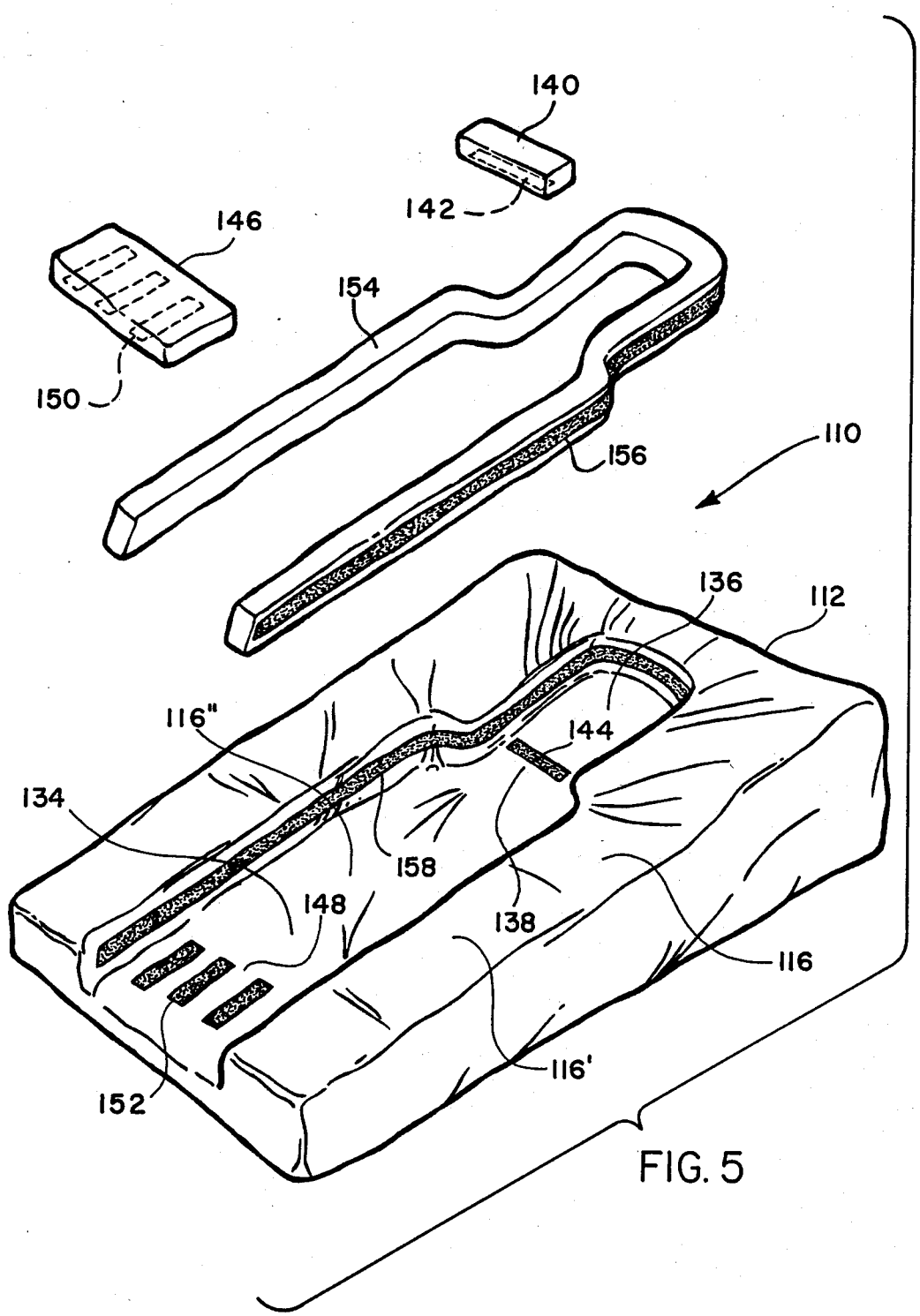
FIG. 5 is an exploded perspective view of another preferred embodiment of the supine support device of the present invention.

Referring now to the FIG. 5, an alternative embodiment of the supine support pillow of the present invention is indicated generally at 110, the pillow including a wedge-shaped main body 112 of generally the same construction as that of the pillow 10 of FIGS. 1-4. According to this embodiment, however, the pillow 110 is provided with a plurality of supplementary support members each of which is selectively attachable to and detachable from the upper surface 116 of the main body 112 to enable the user to selectively adjust the size and support characteristics of the recessed user support region 116" to suit the user's own particular needs and desires. Specifically, instead of the permanent cervical support 38 of the first embodiment, a generally rounded cervical support member 140 is provided for selective attachment to and detachment from the cervical support area 138 of the recessed region 116" by mating fastener strips 142,144, e.g. VELCRO type fastener strips, affixed respectively along the cervical support cushion 140 and across the cervical support area 138. The fastener strips 142,144 are sufficiently dimensioned to enable the selective positioning of the cervical support cushion 140 within a reasonable range of possible positions at the cervical support area 138 for proper positioning of the cushion 140 to underlie the user's neck for optimal cervical support. Similarly, a rectangular lumbar support cushion 146 is selectively attachable to and detachable from the lumbar area 148 of the recessed user support region 116" by a plurality of mating fastener strips 150,152 affixed to the lumber support cushion 146 and to the lumbar area 148 of the upper body surface 116 for selective positioning of the lumbar cushion 146 to provide comfortable support for the user's lower back.

As an alternative to the aforementioned possibility of constructing the pillow 10 in varying sizes, an elongated auxiliary cushion member 154 may be provided for selective attachment to and detachment from the upper surface 116 of the main body 112 to extend substantially along the full extent of the marginal region 116' adjacent the recessed user support region 116" so as to define the torso and head support areas 134,136 of a smaller size, thereby enabling the selective adjustment of the size of the recessed user support region 116" to be compatible with users of a variety of ages and sizes. The auxiliary cushion member 154 is provided with a fastener strip 156 affixed to one side of the cushion member 154 along substantially its full length and the marginal region 116' of the upper body surface 116 is provided with a mating fastener strip 158 affixed along the generally upright surface of the marginal region 116' inwardly facing the recessed region 116", to facilitate attachment of the auxiliary cushion member 154 in place as described. As necessary or desirable, auxiliary cushion members 154 may be constructed of varying cross-sectional thicknesses for selective alternative attachment to the main body 112 to enable the size of the recessed region 116" to be selectively changed among a variety of differing possible sizes. In this manner, one main body 112 may be adapted to accommodate virtually all possible users. This is of particular advantage for the orthodontic treatment of children and adolescents in that the size of the recessed region 116" may be enlarged as the patient grows in size. The selective positionability of the cervical and lumbar support cushions 140,146 compatibly permits these cushions to be adjustably positioned with respect to the growth of the patient.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiment, adaptations, variations, modifications and equivalent arrangements, the present invention being limited only by the claims appended hereto and the equivalents thereof.

I claim:

1. A pillow for the therapeutic treatment and prevention of malocclusion of the teeth, characterized in that said pillow constrains a user to lie in a supine position during sleeping, resting and similar periods of general activity, said pillow comprising a generally wedge-shaped main body adapted for supporting a user's torso and head when supine, said main body having a lower surface for resting disposition on a generally horizontal support surface suitable for sleeping and resting such as a mattress, bed or the like and a cushioned upper surface extending at an acute angle with respect to said lower surface for disposition at an upward incline with respect to horizontal, said upper surface being formed with a relatively elevated marginal region bordering a relatively recessed user support region having a torso support area, a head support area and a cervical support area intermediate said torso and head support areas relatively elevated therefrom, said user support region generally conforming in shape to the human torso and head to enable a user to comfortably lie supine with the user's torso and head within said recessed torso and head support areas with said elevated marginal region acting to resist any tendency of the user to turn from the supine position and with said cervical support area providing cervical support to the user's neck, said main body having a first substantially wedge-shaped body member for forming said lower surface, a second substantially planar body member secured in superposed relation to said first body member for forming said user support region, a third substantially planar body member secured in superposed relation to said second body member and having an opening formed therethrough in the general shape of the human torso and head for forming said elevated marginal region and defining said recessed user support region, and a fourth body member secured in superposed relation to said second body member intermediate said torso and head support areas of said user support region for forming said cervical support area, thereby promoting natural development of the occlusion of the user's teeth by deterring the user from sleeping and resting in prone and sidewise positions wherein the user's jaws may assume an unnatural relationship.

2. A pillow for the therapeutic treatment and prevention of malocclusion of the teeth according to claim 1 and characterized further in that said cervical support area comprises a cervical support member selectively attachable to and detachable from said recessed user support region of said upper surface of said main body at said cervical support area.

3. A pillow for the therapeutic treatment and prevention of malocclusion of the teeth according to claim 2 and characterized further in that said cervical support member is selectively positionable within said cervical support area.

4. A pillow for the therapeutic treatment and prevention of malocclusion of the teeth according to claim 2 and characterized further in that said cervical support member and said upper surface of said main body have mating fastener members thereon for selective attachment to one another.

5. A pillow for the therapeutic treatment and prevention of malocclusion of the teeth according to claim 1 and characterized further by a lumbar support member selectively attachable to and detachable from said recessed user support region of said upper surface of said main body at a lumbar support portion of said torso support area.

6. A pillow for the therapeutic treatment and prevention of malocclusion of the teeth according to claim 5 and characterized further in that said lumbar support member is selectively positionable within said lumbar support portion of said torso support area.

7. A pillow for the therapeutic treatment and prevention of malocclusion of the teeth according to claim 5 and characterized further in that said lumbar support member and said upper surface of said main body have mating fastener members thereon for selective attachment to one another.

8. A pillow for the therapeutic treatment and prevention of malocclusion of the teeth according to claim 1 and characterized further by at least one auxiliary cushion member selectively attachable to and detachable from said upper surface of said main body within said recessed user support region at said marginal region for selectively adjusting the size of said user support region to be compatible with users of varying sizes.

9. A pillow for the therapeutic treatment and prevention of malocclusion of the teeth according to claim 8 and characterized further in that said auxiliary cushion member is sufficiently elongate to extend substantially along the full extent of said marginal region adjacent said user support region.

10. A pillow for the therapeutic treatment and prevention of malocclusion of the teeth according to claim 9 and characterized further in that said auxiliary cushion member and said upper surface of said main body have mating fastener members thereon for selective attachment to one another.

11. A pillow for the therapeutic treatment and prevention of malocclusion of the teeth, characterized in that said pillow constrains a user to lie in a supine position during sleeping, resting and similar periods of general activity, said pillow comprising a generally wedge-shaped main body adapted for supporting a user's torso and head when supine, said main body having a lower surface for resting disposition on a generally horizontal support surface suitable for sleeping and resting such as a mattress, bed or the like and a cushioned upper surface extending at an acute angle with respect to said lower surface for disposition at an upward incline with respect to horizontal, said upper surface being formed with a relatively elevated marginal region bordering a relatively recessed user support region having a torso support area and a head support area generally conforming in shape to the human torso and head to enable a user to comfortably lie supine with the user's torso and head within said recessed torso and head support areas with said elevated marginal region acting to resist any tendency of the user to turn from the supine position, and at least one auxiliary cushion member selectively attachable to and detachable from said upper surface of said main body within said recessed user support region at said marginal region for selectively adjusting the size of said user support region to be compatible with users of varying sizes, said auxiliary cushion member being sufficiently elongated to extend substantially along the full extent of said marginal region adjacent said user support region, thereby promoting natural development of the occlusion of the user's teeth by deterring the user from sleeping and resting in prone and sidewise positions wherein the user's jaws may assume an unnatural relationship.

12. A pillow for the therapeutic treatment and prevention of malocclusion of the teeth according to claim 11 and characterized further in that said auxiliary cushion member and said upper surface of said main body have mating fastener members thereon for selective attachment to one another.

* * * * *